United States Patent
Christ, Jr. et al.

(10) Patent No.: US 7,559,233 B2
(45) Date of Patent: Jul. 14, 2009

(54) METHOD FOR SURFACE REPLICATION VIA THERMOPLASTIC MEDIA

(75) Inventors: Robert J. Christ, Jr., Brentwood, NY (US); Jerrell A. Nardiello, Hicksville, NY (US); John M. Papazian, Great Neck, NY (US); John Steven Madsen, Commack, NY (US)

(73) Assignee: Northrop Grumman Corporation, Los Angeles, CA (US)

( * ) Notice: Subject to any disclaimer, the term of this patent is extended or adjusted under 35 U.S.C. 154(b) by 356 days.

(21) Appl. No.: 11/654,945

(22) Filed: Jan. 18, 2007

(65) Prior Publication Data

US 2008/0173078 A1 Jul. 24, 2008

(51) Int. Cl.
*G01N 19/08* (2006.01)
(52) U.S. Cl. ...................................... 73/104
(58) Field of Classification Search ............ 73/104
See application file for complete search history.

(56) References Cited

U.S. PATENT DOCUMENTS

| | | | |
|---|---|---|---|
| 4,289,821 A | 9/1981 | Gray, III et al. |
| 4,322,450 A | 3/1982 | Gray, III et al. |
| 4,427,732 A | 1/1984 | Gray, III et al. |
| 4,560,578 A | 12/1985 | Freeman |
| 2003/0147326 A1* | 8/2003 | Wilkinson et al. | 369/59.25 |
| 2005/0157628 A1* | 7/2005 | Wilkinson et al. | 369/275.1 |

OTHER PUBLICATIONS

SPI Replicating Tapes and Sheets. Structure Probe, Inc. Copyright 1996-2007. Jul. 2, 2007. <http://www.2spi.com/catalog/submat/cellulose-acetate-replicating-tape-sheets.shmtl> 4 pages.
President SEM Replication Kit for High Resolution SEM Replicas. Ted Pella, Inc. Copyright 1996-2007. Jul. 2, 2007. <http://www.tedpella.com/replicat_html/44870.htm> 2 pages.
SPI Chem™ Wet Surface Replica Kit. Structure Probe, Inc. Copyright 1995-2007. Jul. 2, 2007. <http://www.2spi.com/catalog/spec_prep/wet_rep_kits.shmtl> 5 pages.

(Continued)

*Primary Examiner*—Akm E Ullah
*Assistant Examiner*—Rodney T Frank
(74) *Attorney, Agent, or Firm*—Stetina Brunda Garred & Brucker

(57) ABSTRACT

A method of inspecting a specimen under test may comprise the step of disposing melted thermoplastic media onto a surface under test of the specimen under test, maintaining a constant temperature of the specimen under test at or about room temperature wherein the temperature of the specimen under test is initially lower than the temperature of the melted thermoplastic media, hardening the melted thermoplastic media to produce a replica with imperfections molded into a mating surface of the replica, and inspecting the mating surface of the replica for unsatisfactory or satisfactory imperfections in the specimen under test.

9 Claims, 2 Drawing Sheets

OTHER PUBLICATIONS

Replication Materials. Ted Pella, Inc. Copyright 1996-2007. Jul. 2, 2007. <http://www.tedpella.com/replicat_html/44840.htm> 2 pages.

Replicating Films and Transport Boxes. Electron Microscopy Sciences. Copyright 2003-2007. Jul. 2, 2007. <http://www.emsdiasum.com/microscopy/products/materials/replicating.aspx> 6 pages.

3M™ ESPE™ Impregum™ Impression System Materials. 3M. Copyright 2007. Jul. 2, 2007. <http://solutions.3m.com/wps/portal/3M/en_US/3M-ESPE/dental-professionals/products/catalog/online/?PC_7_0_3DVS_nid=FP0CMGQ1GTbe8KFKMTRV4Vgl> 2 pages.

* cited by examiner

METHOD FOR SURFACE REPLICATION VIA THERMOPLASTIC MEDIA

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates to a method of inspecting a surface of a specimen to inspect for unsatisfactory imperfections in the specimen under test.

Component parts of a machine (e.g., airplane, space shuttle, automobile, etc.) need to be inspected for imperfections that may be unsatisfactory for the designated purpose of the part. For example, a component part of,an airplane may have to be inspected for cracks, scratches and other imperfections. The cracks, scratches, and other imperfections may cause the component part to fail during use or operation of the airplane. Such failure of the component part may be mission critical in that although human life may not be in danger if the component part fails, the airplane may not be able to accomplish the mission at hand. Alternatively, failure of the component part may threaten life if unsatisfactory imperfections, scratches, or cracks are in the component part. Accordingly, certain parts of a device should be tested, especially if they are mission critical parts or safety critical parts.

When inspecting these component parts, it may often be necessary to take microscopic images of surfaces of the component parts. The surface to the inspected may be an exposed flat surface, a hole or have other features. The various configurations of the surface to be inspected may make inspection of the surface difficult. By way of example and not limitation, a hole in the component part may be difficult to inspect via a microscope. The reason is that the surface of the hole may not be able to fit under the microscope. Additionally, the hole may be awkward to inspect via the microscope.

In the prior art, instead of directly inspecting the component part for inspection, a replica of the surface to be inspected of the component part may be made. The replica may be smaller than the component part and conveniently disposed under the microscope. One prior art method of making the replica utilizes an acetate film softened with a solvent. Once the acetate film is softened, the acetate film is placed over the surface to be inspected and allowed to harden. When the acetate film is placed over the surface, the acetate film conforms to the surface of the component part. Any imperfection, scratch or cracks in the surface is molded into the acetate film. Once hardened, the film is removed from the component part and the film is inspected for any imperfections, scratches and cracks. Unfortunately, acetate replicas may be time consuming and require skill and training.

Another method of making replicas utilize a resin. The resin is injected into the hole or onto a surface to be inspected. The imperfections, scratches and cracks in the surface to the inspected are molded into the resin. The resin is then hardened and inspected. The resin may be silicone or a dental casting media. Unfortunately, the casting method may be time consuming because the resin may not cure quickly.

Accordingly, there is a need in the art for an improved method of making a replica to inspect the surface to the inspected for unsatisfactory imperfections.

BRIEF SUMMARY

The method and device disclosed herein addresses the needs discussed above, discussed below and those that are known in the art.

The method of inspecting a surface of a specimen for unsatisfactory imperfections may comprise the step of disposing melted thermoplastic media on the surface under test. The melted thermoplastic media may be disposed on the surface under test via a thermoplastic media applicator. The method may comprise the step of maintaining a constant temperature of the specimen under test while the melted thermoplastic media is disposed on the surface under test via a simple delivery mechanism. The method may also comprise the step of maintaining the specimen under test at or about room temperature. As such, when the melted thermoplastic media is disposed on the surface under test, the temperature of the melted thermoplastic media approaches the temperature of the specimen under test thereby hardening the melted thermoplastic media. Beneficially, the hardened thermoplastic media has a mating surface with imperfections of the surface under test molded into the mating surface and the replica is easily disbondable or removeable from the specimen under test.

The method may further comprise the step of colorizing the mating surface of the replica so as to make the imperfections molded into the mating surface more easily inspectable.

The thermoplastic media applicator may comprise a container for containing solid or solidified thermoplastic media, a heater for melting the solid thermoplastic media, and a pump for flowing melted thermoplastic media from the container through a hose and out of a dispensing nozzle. The dispensing nozzle may have a trigger which is operative to activate or deactivate the pump. Moreover, the thermoplastic media applicator may further comprise a separate heat sink attachable to the specimen under test for maintaining the specimen under test at a constant temperature, preferably, room temperature.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Referring now to the figures, the method and device described herein is directed to a method and device for producing a replica 10 (see FIGS. 2 and 3) of surface under test 12 of a specimen under test 14 such that if the specimen under test 14 cannot be conveniently inspected with a microscope 16 (i.e., the specimen under test 14 is too large for the microscope 16 or the surface under test is not readily exposed), the replica 10 which is a mirror image of the surface under test 12 is smaller, and the exposed surface of the replica can be conveniently inspected via the microscope 16.

Figure 1:
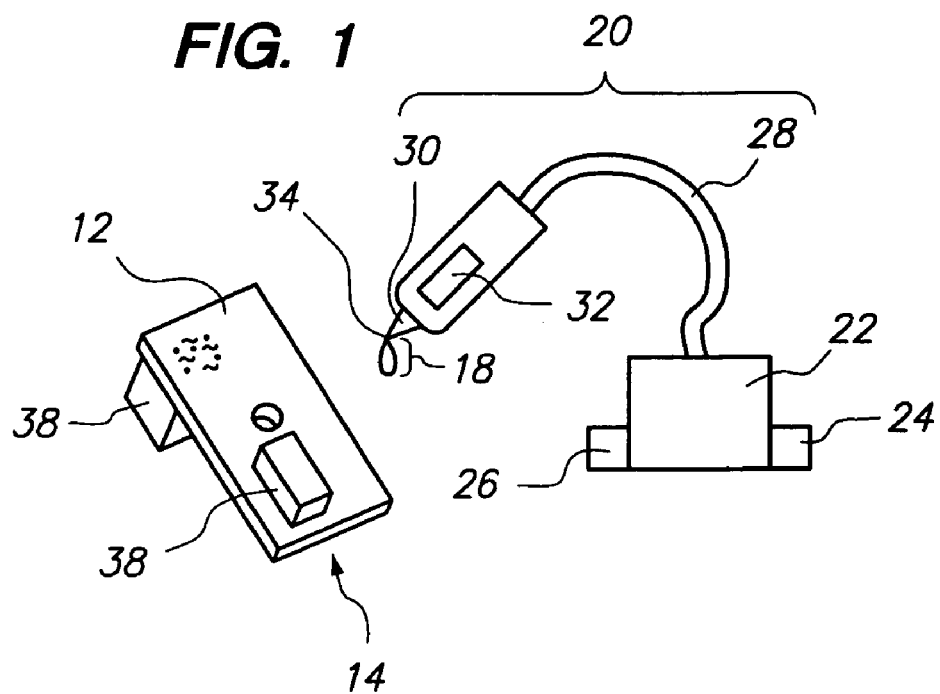
FIG. 1 is an illustration of a thermoplastic media applicator, specimen under test, and a cooling device.

The specimen under test 14 may be any type of part such as an airplane part, space shuttle part, machine part, component part of a device, or the like. To produce the replica 10 of the surface under test 12 of the specimen under test 14, a thermoplastic media 18 is disposed on the surface under test 12 via a thermoplastic media applicator 20. As shown in FIG. 1, the thermoplastic media applicator 20 may comprise a container 22 in heat communication with a heater 24. Initially, the thermoplastic media 18 may be provided in a solid form (e.g., pellet, balls, block etc.). The thermoplastic media 18 may be disposed in the container 22. The heater 24 may be activated so as to transfer heat into the container 22 and liquefy or melt the thermoplastic media 18 disposed therein 22. The applicator 20 of the thermoplastic media may also comprise a pump 26 for flowing melted thermoplastic media 18 through an elongate hose 28 and a dispensing nozzle 30. The pump 26 may be activated via a trigger 32 located on the dispensing nozzle 30. In use, a technician may grasp the dispensing nozzle 30 and place a tip 34 of the dispensing nozzle 30 closely adjacent to the surface under test 12. The technician may then depress the trigger 32 to activate pump 26. Melted thermoplastic media 18 is then flowed through the hose 28 and out of the dispensing nozzle 30. The melted thermoplastic media is disposed on the surface under test 12 to a sufficient degree so as to cover the entire surface under test 12.

After the melted thermoplastic media 18 covers the entire surface under test 12, the melted thermoplastic media 18 is allowed to harden. While the melted thermoplastic media 18 is disposed on the surface under test 12, the melted thermoplastic media conforms to the imperfections of the surface under test 12 due to machining, normal use, other fabricating processes, etc. After the thermoplastic media 18 has hardened, the hardened thermoplastic media 18 which may now be referred to as the replica 10 may be removed from the specimen under test 14. The mating surface 36 of the replica 10 may have a mirror image of the imperfections of the surface under test 12. Beneficially, the replica 10 covers only a portion of the specimen under test 14, and, as such the replica 10 may typically be smaller compared to the specimen under test 14. The replica 10 may then be conveniently placed under a microscope 16 for inspecting the mating surface 36 of the replica 10 for any unsatisfactory imperfection such as cracks, etc.

Preferably, the surface under test 12 is maintained at a temperature lower than the temperature of the melted thermoplastic media 18 while the melted thermoplastic media 18 is being disposed onto the surface under test 12. Preferably, the surface under test is maintained at or about room temperature, whereas the thermoplastic media 18 is ejected out of the dispensing nozzle 30 at or about a melting temperature of the thermoplastic media 18. To maintain the surface under test 12 at or about the room temperature, a heat sink 38 may be placed in heat communication with the surface under test 12. By way of example and not limitation, the heat sink 38 may be screwed onto the specimen under test 14 or adhere to the specimen under test 14 with a heat conductive adhesive. The heat sink 38 is a type of passive cooling device. Other types of passive cooling devices are also contemplated within the scope of this disclosure. Alternatively, an active cooling device such as a thermo electric heat pump may be placed in heat communication with the surface under test 12. Other types of active cooling devices are also contemplated such as a fan blowing over a surface adjacent to the surface under test 12 or over the heat sink 38.

When the melted thermoplastic media 18 is disposed on the surface under test 12, heat is transferred from the melted thermoplastic media 18 to the specimen under test 14. The cooling device, or as in the example above, the heat sink 34 may sufficiently maintain the temperature of the specimen under test 14 at or about a constant temperature, preferably, room temperature. The temperature of the specimen under test 14 may be characterized as being sufficiently maintained at a constant temperature (e.g., room temperature) if the mating surface 36 of the melted thermoplastic media 18 is able to conform to the imperfections of the surface under test 12 and the melted thermoplastic media when hardened (i.e., cured) is not excessively bonded to the surface under test 12. The hardened thermoplastic media 18 is excessively bonded to the surface under test 12 if the imperfections of the surface under test 12 molded into the mating surface 36 of the replica 10 is destroyed when the hardened thermoplastic media 18 is removed from the specimen under test 14. By way of example and not limitation, the imperfections molded into the replica 10 is not sufficiently preserved or destroyed if the replica 10 when removed from the specimen under test 14 is torn or if a portion of the mating surface 36 of the replica 10 sticks onto the surface under test 12 or if the mating surface 36 of the replica 10 is delaminated.

By way of example and not limitation, the thermoplastic media may be ABS (acrylo-nitrilebutadienestyrene), nylon, polypropylene, various acrylics, SAN (styrene acrylonitril) as well as other types of similar thermoplastic materials. The melting temperature of the thermoplastic media may be about 180 degrees Fahrenheit to about 350 degrees Fahrenheit.

The cooling device discussed above and the step of maintaining a constant temperature in the specimen under test 14 promotes easy disbonding of the hardened thermoplastic media 18 or replica 10 from the specimen under test 14 such that the hardened thermoplastic media 18 or replica 10 does not tear, delaminate or otherwise make unusable the imperfections molded into the hardened thermoplastic media 18 or replica 10 when the thermoplastic media 18 or replica 10 is removed from the specimen under test 14.

In certain circumstances, the mating surface 36 of the replica may not be easily viewable via a naked human eye, microscope, electron microscope or other inspection device. To make the mating surface 36 more easily inspectable, the mating surface 36 may be sputtered with a thin metallic coating such as gold, or other like material. The sputtered gold creates a contrasting or shadowing layer that will allow the mating surface 36 to be imaged in an inspection device such as an electron microscope 16. Alternatively, to make the mating surface 36 more easily inspectable, colorant such as carbon black may be mixed with the thermoplastic media 18. The colorant enhances the imperfections molded into the mating surface 36 of the replica 10.

Figure 2:
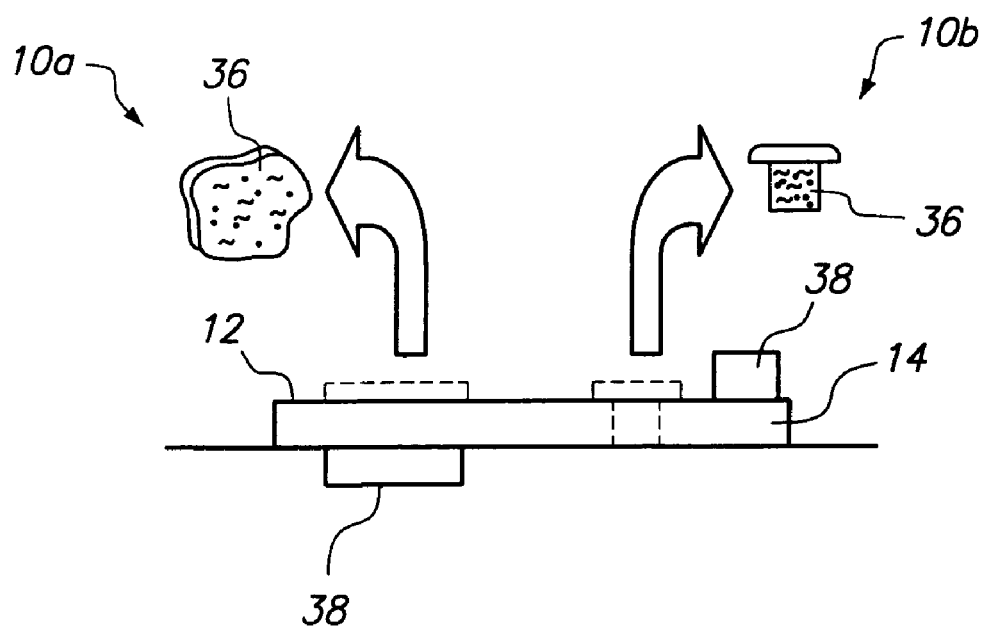
FIG. 2 is an illustration of a replica removed from the specimen under test.
Figure 3:
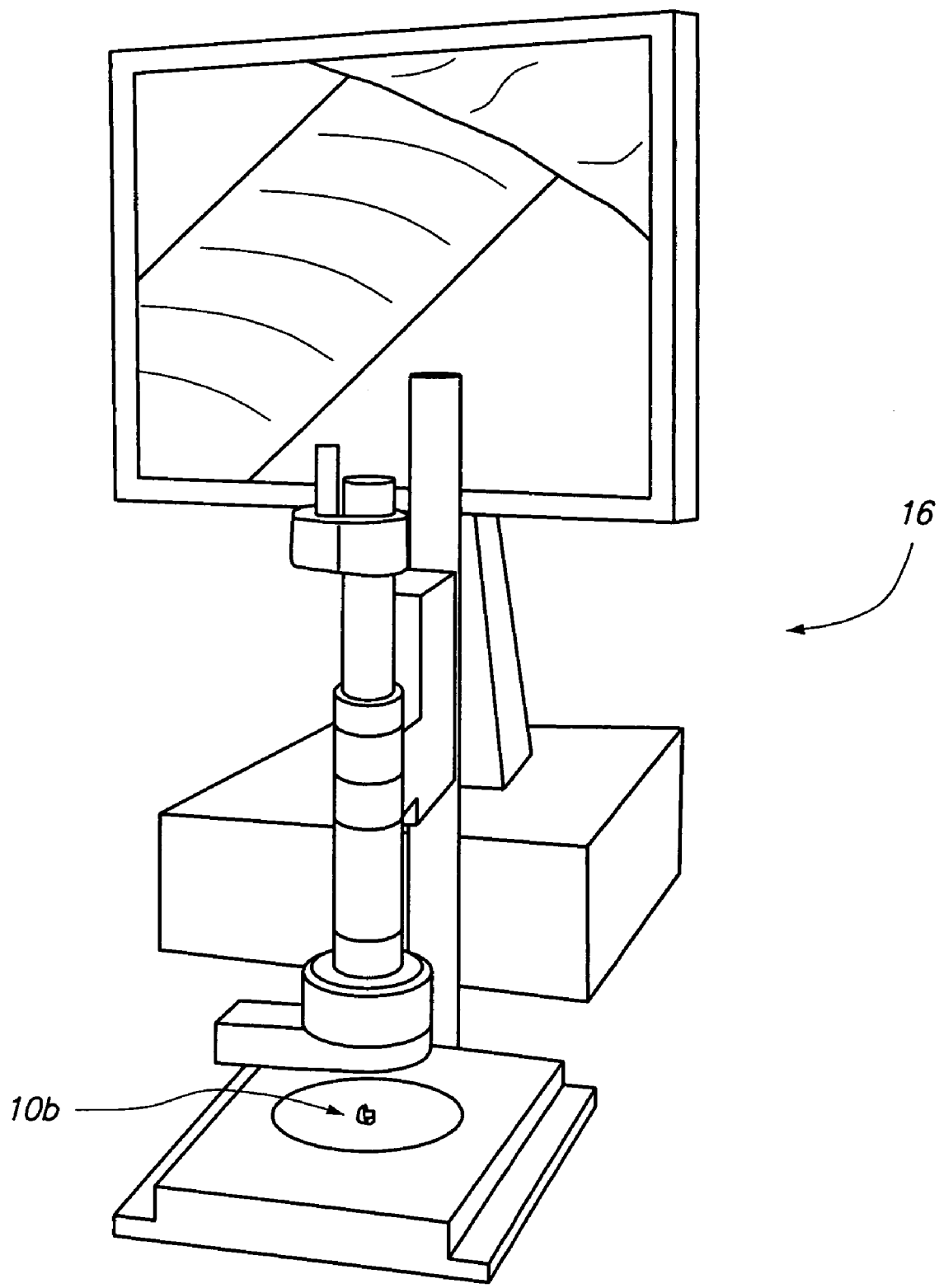
FIG. 3 is an illustration of an inspection device inspecting the replica shown in FIG. 2, and an enlarged view of the mating surface with imperfections of the surface under test molded into the mating surface.

As shown in FIG. 2, the surface under test 12 may be an exposed surface of the specimen under test 14. In the event that the specimen under test 14 is too large to be disposed under a microscope 16, the replica 10 of the surface under test 12 may be fabricated. The replica may be small enough such that the replica 10 may be disposed under the microscope 16 to inspect the mating surface 36 for any unsatisfactory imperfections in the surface under test 12. Moreover, the surface under test 12 may be a hole in the specimen under test 14. The hole may be difficult to inspect because the microscope may be able to obtain a direct view of the surface under test 12. The replica 10 of the surface of the hole may be fabricated. After the replica 10 is removed from the hole, the exposed surface of the replica 10 which represents the surface under test 12 of the specimen under test 14 may be conveniently disposed under a microscope. The microscope has a direct view of the mating surface to detect any unsatisfactory imperfections in the surface under test 12 of the specimen under test 14.

In an aspect of the method and device for inspecting a surface under test 12, the same may be utilized to determine whether the surface under test 12 has an unsatisfactory crack, scratch and also be able to determine the depth and spacing of such crack and scratch.

The method of inspecting a surface under test may comprise the steps of providing a specimen under test 14, disposing melted thermoplastic media 18 onto the surface under test 12, maintaining a constant temperature of the specimen under test 14. More preferably, the specimen under test 14 is maintained at a temperature at or about room temperature or ambient temperature. The method may comprise the step of hardening the melted thermoplastic media 18 by lowering its temperature to fabricate the replica 10. The method may also comprise the step of removing the replica 10 from the specimen under test 14. Lastly, the mating surface 36 of the replica 10 may be inspected for unsatisfactory imperfections of the surface under test 12 via an inspection device such as a microscope 16.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for inspecting a surface of a specimen for unsatisfactory imperfections in the surface under test, the method comprising the steps of:
    disposing melted thermoplastic media on the surface under test;
    hardening the thermoplastic media to produce a replica having a mating surface with imperfections of the surface under test molded into the mating surface;
    maintaining a constant temperature of the specimen under test;
    inspecting the imperfections molded into the mating surface;
    rejecting the specimen under test if the imperfection molded into the mating surface is unsatisfactory; and
    accepting the specimen under test if the imperfection molded into the mating surface is satisfactory.

2. The method of claim 1 wherein the step of disposing melted thermoplastic media onto the surface under test is accomplished via thermoplastic media applicator.

3. The method of claim 1 wherein the step of maintaining a constant temperature is performed during the disposing step and the hardening step.

4. The method of claim 1 wherein the step of maintaining a constant temperature of the specimen under test is performed with a heat sink, a passive cooling device or an active cooling device.

5. The method of claim 1 wherein the constant temperature of the maintaining step is at or about room temperature.

6. The method of claim 1 further comprising the step of colorizing the mating surface of the replica for making the imperfections molded into the mating surface more readily inspectable.

7. The method of claim 6 wherein the step of colorizing comprises the step of sputtering a thin metallic coating on the mating surface.

8. The method of claim 7 wherein the thin metallic coating is fabricated from gold.

9. The method claim 6 wherein the colorizing step comprises the step of mixing a colorant into the thermoplastic media.

* * * * *